(12) United States Patent
Ott et al.

(10) Patent No.: US 11,172,819 B2
(45) Date of Patent: Nov. 16, 2021

(54) SINGLE POINT WIRELESS BIOPOTENTIAL MONITORING SYSTEMS AND METHODS

(71) Applicant: Freedom Cardio LLC, Kirkwood, MO (US)

(72) Inventors: James E Ott, Kirkwood, MO (US); Jon Barron, Valley Center, CA (US)

(73) Assignee: Freedom Cardio LLC, Kirkwood, MO (US)

( * ) Notice: Subject to any disclaimer, the term of this patent is extended or adjusted under 35 U.S.C. 154(b) by 227 days.

(21) Appl. No.: 16/179,474

(22) Filed: Nov. 2, 2018

(65) Prior Publication Data
US 2020/0037877 A1    Feb. 6, 2020

Related U.S. Application Data

(60) Provisional application No. 62/712,609, filed on Jul. 31, 2018.

(51) Int. Cl.
| | |
|---|---|
| *A61B 5/00* | (2006.01) |
| *H04W 56/00* | (2009.01) |
| *A61B 5/341* | (2021.01) |
| *A61B 5/25* | (2021.01) |
| *A61B 5/301* | (2021.01) |

(52) U.S. Cl.
CPC ............ *A61B 5/0006* (2013.01); *A61B 5/341* (2021.01); *H04W 56/0015* (2013.01); *A61B 5/25* (2021.01); *A61B 5/301* (2021.01)

(58) Field of Classification Search
CPC ............... H04W 56/0015; A61B 5/006; A61B 5/04011; A61B 5/0408; A61B 5/04282; A61B 5/0002

See application file for complete search history.

(56) References Cited

U.S. PATENT DOCUMENTS

| | | |
|---|---|---|
| 6,441,747 B1 | 8/2002 | Khair et al. |
| 6,496,705 B1 | 12/2002 | Ng et al. |
| 6,643,541 B2 | 11/2003 | Mok et al. |
| 8,838,218 B2 | 9/2014 | Khair |
| 8,937,509 B2 | 1/2015 | Xu et al. |
| 9,571,907 B2 | 2/2017 | Slack |
| 2002/0045836 A1 | 4/2002 | Alkawwas |

(Continued)

OTHER PUBLICATIONS

Nabil Hamza, Lazhar Khriji, Rached Tourki, "Rejection of Common-Mode Voltages in ECG Signal by Removing the Ground Electrode", International Journal of Scientific & Engineering Research, Feb. 2016, vol. 7, Issue 2, ISSN 2229-5518.

*Primary Examiner* — Allen Porter (74) *Attorney, Agent, or Firm* — Husch Blackwell LLP (57) ABSTRACT

Multiple wireless sensor assemblies are individually attached to standard biopotential electrodes, which are placeable on a subject's body at locations for biopotential signal recording. The sensor assemblies, which are electrically isolated, simultaneously measure potential voltages from the body sites in accordance with a synchronization. The measured signals are amplified, digitized, and filtered, and then sent wirelessly to a monitoring system. The monitoring system receives multiple sensor signals and constructs biopotential vectors depending on the placement and number of the sensors. The sensor signals are referenced to a common virtual center bias to synthesize a common mode rejection.

8 Claims, 6 Drawing Sheets

(56) References Cited

U.S. PATENT DOCUMENTS

| | | |
|---|---|---|
| 2010/0056871 A1 | 3/2010 | Govari et al. |
| 2011/0004276 A1* | 1/2011 | Blair .................... A61B 5/6887 |
| | | 607/60 |
| 2015/0201858 A1 | 7/2015 | Ganim et al. |
| 2016/0022161 A1 | 1/2016 | Khair |
| 2016/0213263 A1* | 7/2016 | Felix .................. A61B 5/04087 |
| 2016/0374584 A1 | 12/2016 | Townsend |
| 2017/0055862 A1* | 3/2017 | Youn ................... A61B 5/0006 |
| 2017/0258402 A1* | 9/2017 | Acquista .................. A61B 5/25 |

* cited by examiner

SINGLE POINT WIRELESS BIOPOTENTIAL MONITORING SYSTEMS AND METHODS

CROSS-REFERENCE TO RELATED APPLICATIONS

This application claims priority to U.S. Provisional Application Ser. No. 62/712,609, filed Jul. 31, 2018, the entire disclosure of which is incorporated herein by reference.

FIELD OF INVENTION

The present disclosure relates generally to systems and methods for acquiring and monitoring biopotential measurements of a living subject, such as a patient.

BACKGROUND

Conventional electrocardiogram (EKG) techniques for biopotential measurements typically require multiple electrodes. Each electrode is connected to a wired lead that senses biopotential and connects it to instrumentation amplifiers that perform a differential voltage potential measurement from the measurement sites. The wires extending from such electrodes present a problem for the subjects (e.g., patients) as well as the healthcare personnel to manage. For example, electrode lead wires are time consuming to sort out, provide an opportunity for error of connection to the wrong electrode site, and obstruct patient mobility, posing discomfort. Wired leads also contribute to a low signal-to-noise ratio as they move during patient movements. Although telemetry systems exist, they require the use of wired leads connected to the patient's body to obtain measurements. These telemetry systems amplify and filter such measurements in a unit worn by the patient, which then transmits differential signals to a receiving base station.

Although wireless EKG biopotential monitoring and diagnosis systems exist, these systems require using a common (i.e., identical) reference point between the two measurement points from which a biopotential is recorded. The common reference point causes this common, or global, reference to cancel out when measuring the differential potential between the two inputs. Thus, it does not matter if the potential at the reference is time-varying and not fixed because it cancels out exactly by being a common, or identical, reference point to both inputs. The location of the reference on the body for bipolar measurements does not affect the measurement since it cancels out, therefore it can be located anywhere on the body. By requiring a common reference point, conventional wireless EKG systems require an extra electrode, increase inconvenience, increase weight, and are susceptible to lower signal quality. Furthermore, conventional wireless EKG systems are incompatible with defibrillators.

SUMMARY

Multiple wireless sensor assemblies are individually attached to standard biopotential electrodes, which are placeable on a subject's body at locations for biopotential signal recording. The sensor assemblies, which are electrically isolated, simultaneously measure potential voltages from the body sites in accordance with a synchronization. The measured signals are amplified, digitized, and filtered, and then sent wirelessly to a monitoring system. The monitoring system receives multiple sensor signals and constructs biopotential vectors depending on the placement and number of the sensors. The sensor signals are referenced to a common virtual center bias to synthesize a common mode rejection.

In an aspect, systems and methods include a biopotential monitoring system transmitting a synchronization beacon to a plurality of biopotential sensor assemblies via a wireless communications channel. The biopotential sensor assemblies acquire biopotential signal samples substantially simultaneously based on the synchronization beacon and achieve a virtual common mode rejection for the acquired samples. The biopotential sensor assemblies are electrically isolated from each other. Each biopotential sensor assembly biases its acquired sample to a center voltage and the biopotential sensor assemblies create a virtual center bias that is common to all of the biopotential sensor assemblies. The biopotential monitoring system receives transmissions of biopotential data from each of the biopotential sensor assemblies via the wireless communications channel. The biopotential data digitally represents the acquired biopotential signal samples. The biopotential monitoring system generates complete electrocardiogram vectors from the received biopotential data by, at least in part, referencing the biopotential data to the virtual center bias.

DETAILED DESCRIPTION

In the following detailed description of example embodiments, reference is made to the accompanying drawings that form a part hereof, and in which is shown by way of illustration specific example embodiments in which the inventive subject matter may be practiced. These embodiments are described in sufficient detail to enable those skilled in the art to practice the inventive subject matter, and it is to be understood that other embodiments may be utilized and that logical, mechanical, electrical and other changes may be made without departing from the scope of the inventive subject matter. Aspects of the description herein refer to the drawings more particularly by reference numbers wherein like members refer to like parts.

Some portions of the detailed descriptions which follow are presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities. Unless specifically stated otherwise as apparent from the following discussions, terms such as "processing" or "computing" or "calculating" or "determining" or "displaying" or the like, refer to the action and processes of a computer system, or similar computing device, that manipulates and transforms data represented as physical (e.g., electronic) quantities within the computer system's registers and memories into other data similarly represented as physical quantities within the computer system memories or registers or other such information storage, transmission or display devices.

The description of the various embodiments is to be construed as describing examples only and does not describe every possible instance of the inventive subject matter. Numerous alternatives could be implemented, using combinations of current or future technologies, which would still fall within the scope of the claims. The following detailed description is, therefore, not to be taken in a limiting sense, and the scope of the inventive subject matter is defined only by the appended claims.

Embodiments described herein provide a wireless and programmable biopotential monitoring system for subjects (e.g., patients, etc.) from electrically and physically isolated measurement sites. The embodiments herein enable the removal of the wires that are conventionally used to connected the electrical leads to the electrode sites on the subject's body. In accordance with the descriptions herein, multiple small signal independent measurements can be taken from completely disconnected sites on the subject's body. The resultant measurements can then be combined to reproduce conventional biopotential measurement outputs.

As further described herein, the systems and methods include miniature, low-weight, independent, wireless sensor assemblies that are attachable to conventional electrode patches. The sensor assemblies can detect small signal biopotential (e.g., EKG) measurements and transmit digital signals digitally representing the detected biopotential measurements to an associated biopotential monitoring system that reconstructs them into a biopotential measurement output that resembles conventional outputs. The biopotential monitoring system synchronizes the biopotential measurements collected by the sensor assemblies and applies signal processing algorithms for reconstruction, calibration, and filtration of the signals. The resulting biopotential measurement output can then be communicated to monitoring devices, computing devices, or the like for display and further analysis. In some embodiments, synchronizing the sensor assemblies to simultaneously acquire samples of biopotential signals facilitates a virtual common mode rejection to synthesize the common mode rejection inherent in conventional wired systems. In some embodiments, the sensor assemblies create a common virtual bias that centers the incoming biopotential signals without using the conventional common bias reference signal. As described herein, the incoming signals are biased individually by each sensor assembly because there is no common ground or bias (i.e., each sensor assembly has an independent ground). Because the electrical grounds of the sensor assemblies are not tied together, creating the virtual bias, along with AC coupling, within each sensor assembly enables the digital signals to be referenced to the virtual center bias when reconstructed.

The systems and methods described herein thus provide advantages that include, but are not limited to, (1) enabling interfaces with existing monitoring equipment, personal computing devices, tablet computing devices, and smartphones; (2) enabling greater subject mobility by utilizing wireless communications instead of wired leads; (3) enabling enhanced subject comfort by eliminating all wires connecting the subject's body to monitoring equipment or telemetry boxes; (4) reducing sensitivity of biopotential recording to motion artifacts by eliminating the wires that represent moving components of the biopotential system that typically pull or push the electrode pads and cause signal baseline variation during motion; (5) reducing the time required to connect, sort, organize, and disconnect wired leads; (6) enabling monitoring to occur for extended periods of time; and (7) enabling continuous monitoring of subjects, such as in-home monitoring. Other advantages will be, in part, apparent and, in part, pointed out herein.

Figure 1:
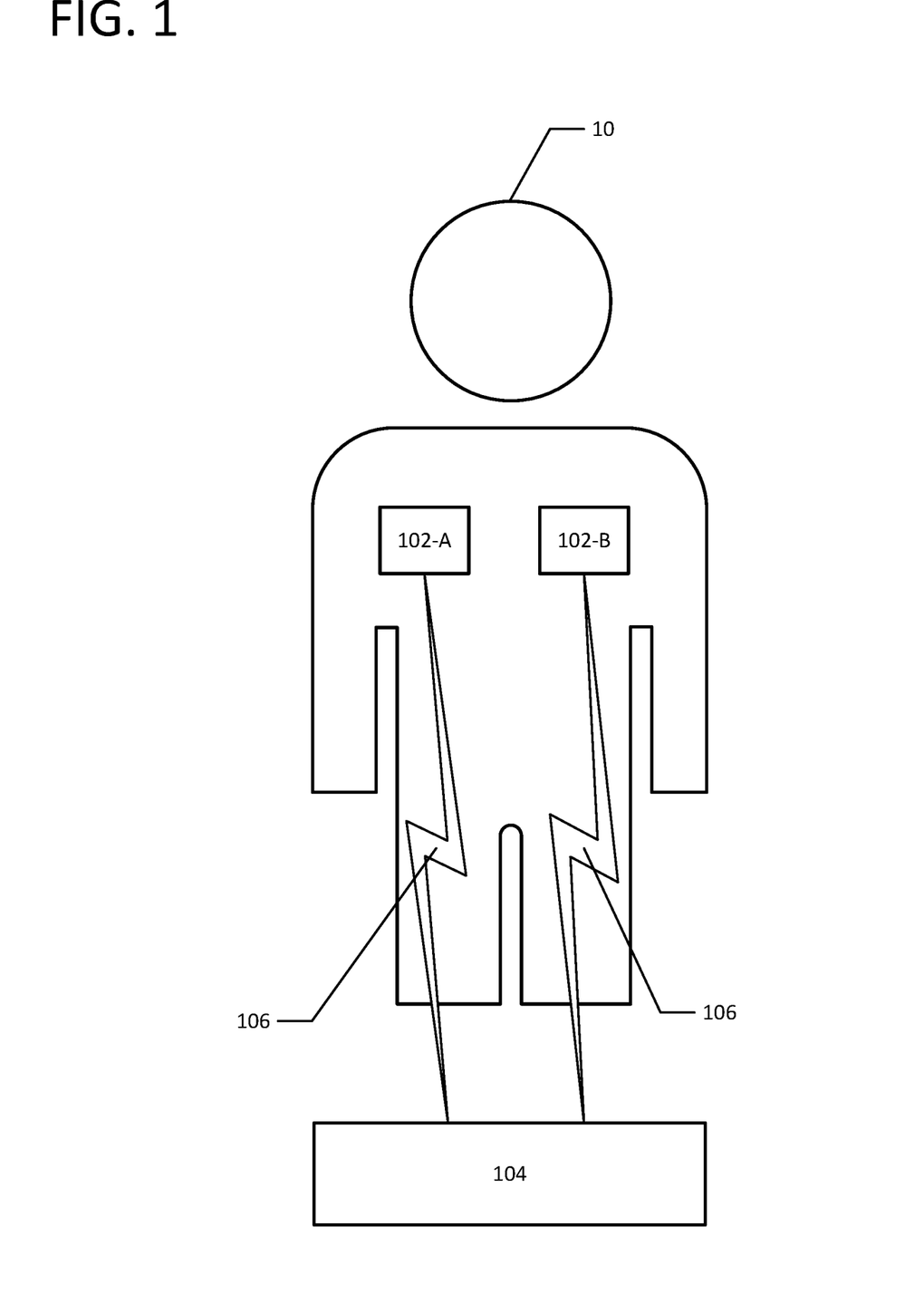
FIG. 1 is a block diagram of a system hereof, according to an example embodiment.

FIG. 1 is a block diagram illustrating a biopotential system 100 for acquiring and monitoring biopotential measurements of a subject 10, such as a patient. As illustrated, system 100 includes a plurality of biopotential sensor assemblies 102 and a biopotential monitoring system 104. The biopotential sensor assemblies 102 and the biopotential monitoring system 104 are communicatively connected via wireless communications channels 106. The biopotential sensor assemblies 102 are isolated (e.g., electrically and physically) from each other. Although the embodiments described herein include a first biopotential sensor assembly 102-A and a second biopotential sensor assembly 102-B, one of ordinary skill in the art will understand that the biopotential system 100 may include more than two biopotential sensor assemblies 102. For example, in some embodiments, the biopotential system 100 may include up to ten or more biopotential sensor assemblies 102. Notably, the biopotential system 100 does not include a sensor assembly for a reference electrode, as commonly required by conventional techniques.

The biopotential sensor assemblies 102 are configured to simultaneously acquire biopotential signal samples from the subject 10 in accordance with a synchronization schedule provided by the biopotential monitoring system 104. As further described herein, synchronizing the acquisition of the biopotential signal samples to occur substantially simultaneously achieves a virtual common mode rejection for the acquired samples. The biopotential sensor assemblies 102 are further configured to center the acquired biopotential signal samples on a virtual center bias value that is common to the plurality of biopotential sensor assemblies 102. Moreover, the biopotential sensor assemblies 102 are configured to convert the biopotential signal samples into digital biopotential data and wirelessly transmit the digital biopotential data to the biopotential monitoring system 104. In some embodiments, the biopotential sensor assemblies 102 are configured to be electrically connected to conventional biopotential electrodes. For example, each biopotential sensor assembly 102 may be attached to biopotential electrodes via a male/female snap connector.

The biopotential monitoring system 104 is configured to generate and wirelessly transmit a synchronization beacon to the biopotential sensor assemblies 102. The biopotential monitoring system 104 is further configured to receive the digital biopotential data wirelessly transmitted by the biopotential sensor assemblies 102 and generate complete biopotential (e.g., electrocardiogram, etc.) vectors from the received biopotential data, including referencing the biopotential data to the virtual center bias.

The wireless communications channels 106 are configured to facilitate the wireless exchange of data between the biopotential sensor assemblies 102 and the biopotential monitoring system 104. In an embodiment, the wireless communications channels comprise a wireless communications network (e.g., a personal area network (PAN), etc.) that conveys data in accordance with the IEEE 802.15 (e.g., Bluetooth®, etc.) protocols. In other embodiments, the wireless communications channels 106 include any medium that allows data to be wirelessly transferred through serial or parallel communication channels.

Figure 2:
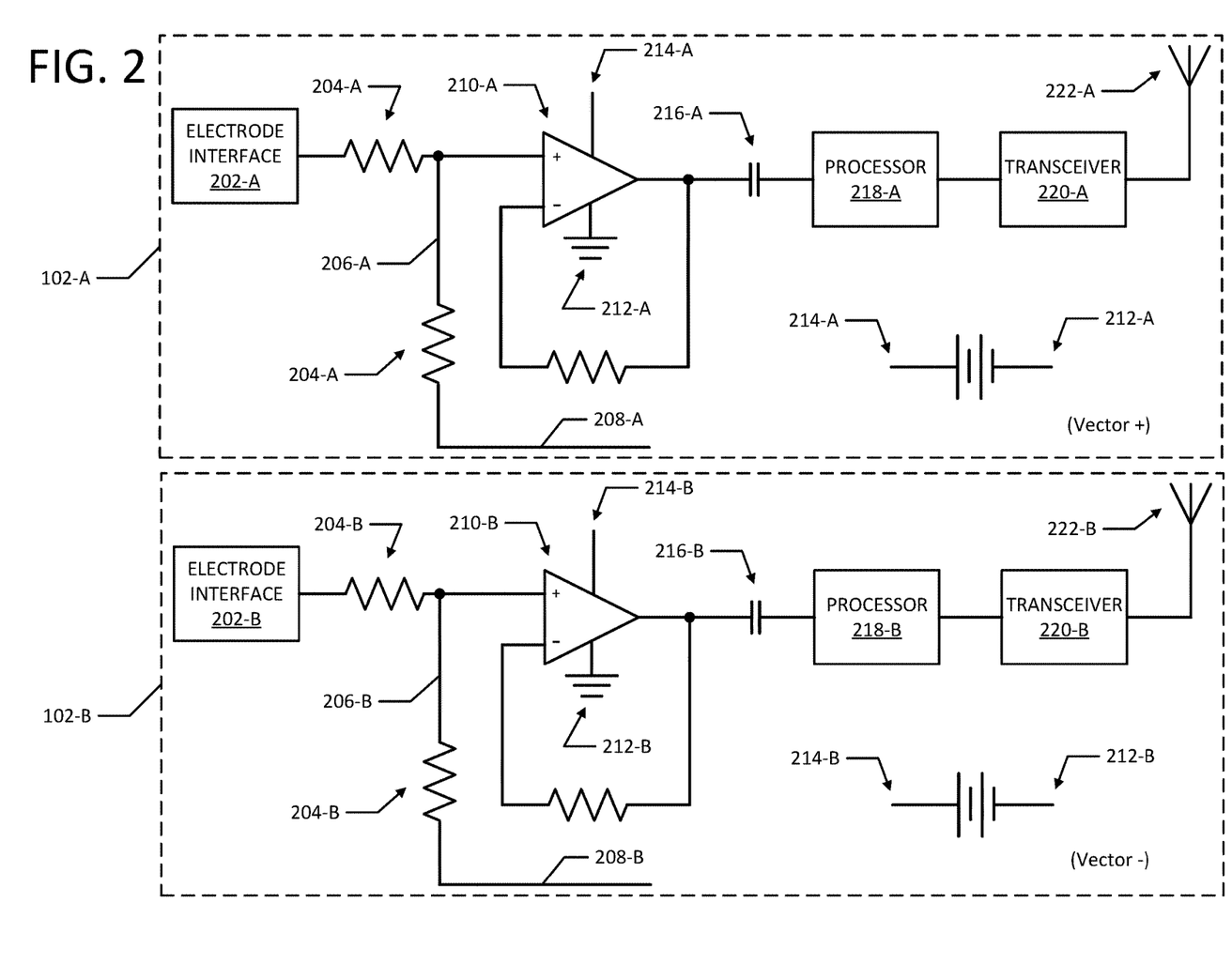
FIG. 2 is a block diagram of biopotential sensor assemblies of the system hereof, according to an example embodiment.

FIG. 2 is a block diagram illustrating the first biopotential sensor assembly 102-A and the second biopotential sensor assembly 102-B. As illustrated, each biopotential sensor assembly 102-A, 102-B includes, respectively, an electrode interface 202-A, 202-B, a plurality of resistors 204-A, 204-B for creating a virtual center 206-A, 206-B, a center bias point 208-A, 208-B, an operational amplifier ("op amp") 210-A, 210-B, an electrical ground 212-A, 212-B, an electric power source 214-A, 214-B, an alternating current (AC) coupling capacitor 216-A, 216-B, a processor 218-A, 218-B, a transceiver 220-A, 220-B, and an antenna 222-A, 222-B.

Referring further to the first biopotential sensor assembly 102-A, the electrode interface 202-A is electrically connected to the plurality of resistors 204-A. A non-inverting input of the op amp 210-A is electrically connected between the plurality of resistors 204-A. The output of the op amp 210-A is electrically connected to an inverting input of the op amp 210-A via another resistor (i.e., in a non-inverting amplifier configuration). The output of the op amp 210 is also electrically connected to a first lead of the AC coupling capacitor 216-A. The other lead of the AC coupling capacitor 216-A is electrically connected to the processor 218-A. The processor 218-A is electrically and/or communicatively connected to the transceiver 220-A, which in turn is electrically and/or communicatively connected to the antenna 222-A. Although the electrical ground 212-A and electric power source 214-A are not connected in FIG. 2 for ease of illustration, one of ordinary skill in the art will understand that the electrical ground 212-A and electric power source 214-A are electrically connected to the components of the first biopotential sensor assembly 102-A. As illustrated in FIG. 2, the components of other biopotential sensor assemblies (e.g., the second biopotential sensor assembly 102-B, etc.) are connected as described above with respect to the first biopotential sensor assembly 102-A. Notably, the first biopotential sensor assembly 102-A and the second biopotential sensor assembly 102-B are electrically isolated from each other (e.g., the assemblies do not share a common ground, etc.). Moreover, each biopotential sensor assembly 102 has its own bias value.

The electrode interface 202 is configured to electrically interface the sensor assembly 102 to a biopotential electrode. For example, conventional a biopotential electrode having a male portion of a snap connector may interface with a sensor assembly 102 via a female portion of the snap connector that comprises the electrode interface 202. The electrode interface 202 receives the biopotential signals collected by the biopotential electrodes.

In an embodiment, the plurality of resistors 204 comprise a voltage divider that is configured to adjust the level of the biopotential signals received by the electrode interface 202 and create a bias for the op amp 210. For example, the resistors 204 in the voltage divider configuration create the virtual center 206 and the center bias point 208. Exemplary resistor values include, but are not limited to, those in the range of about 27.4 kΩ to about 49.9 kΩ and having a precision of at least about 0.1%. In some embodiments, the resistors 204 are within this range to limit the current draw from the electric power source 214 (e.g., a small battery, etc.) and to keep the current flow to the patient's body at acceptable levels. Moreover, in some embodiments, the 0.1% precision of the resistors 204 keeps the ECG signal close to center.

The op amp 210 is configured to amplify the biopotential signals received by the electrode interface 202. In an exemplary embodiment, the op amp 210 amplifies the biopotential signals by a factor of at least about four.

The electric power source 214 is configured to supply electric power to the electronic components of the biopotential sensor assembly 102. The electrical ground 212 is the common return path for the electric current within the circuit of each biopotential sensor assembly and is the reference point from which voltages are measured within the circuit. The electrical ground 212 of each biopotential sensor assembly 102 is electrically isolated from the electrical grounds of other biopotential sensor assemblies 102. In other words, the biopotential sensor assemblies 102 of the biopotential system 100 do not share a common ground. An exemplary electric power source includes, but is not limited to, a battery, such as a lithium polymer (LiPo) battery.

The AC coupling capacitor 216 is configured to remove (e.g., filter, etc.) direct current (DC) components from the amplified biopotential signals. For example, the AC coupling capacitor 216 isolates the wandering signal from DC offsets caused patient movements, electrode conduction changes, and the like. Exemplary capacitor values include, but are not limited to, 0.1 µF low equivalent series inductance (ESL) ceramic ±1%.

The processor 218 is configured to reduce the continuous-time biopotential signals to a discrete-time signal (i.e., sample the biopotential signals). In some embodiments, the processor 218 includes an analog-to-digital converter (ADC). The processor 218 is further configured to receive synchronization beacons from the biopotential monitoring system 104, sample the biopotential signals in accordance with the received beacons, generate data packets including the sampled data, and send acknowledgements and the data packets to the biopotential monitoring system 104, as further described herein. An exemplary processor includes, but is not limited to, one having extreme low power with multiple power saving functions.

The transceiver 220 is configured to combine the digital signals/data packets generated by the processor 218 with a radio frequency (RF) signal and apply the modulated signal to the antenna 222, which radiates the energy of the RF signal as radio waves (e.g., transmissions to an antenna of the biopotential monitoring system 104, etc.). The transceiver 220 is further configured to receive alternating currents received from the antenna 222, which is configured to intercept radio waves (e.g., receiving transmissions from an antenna of the biopotential monitoring system 104, etc.) and convert them into the alternating currents. The transceiver 220 is configured to extract information/data from the alternating currents. Although embodiments herein are described with respect to radio waves, one of ordinary skill in the art will understand that transceivers and antennas configured to transmit and receive other types of electromagnetic waves (e.g., microwaves, infrared, etc.) are within the scope of the invention. An exemplary transceiver includes, but is not limited to, one operating at a low-power, short-range 2.4

GHz multiprotocol and an exemplary antenna includes, but is not limited to, a printed circuit board (PCB)-type antenna.

Figure 3:
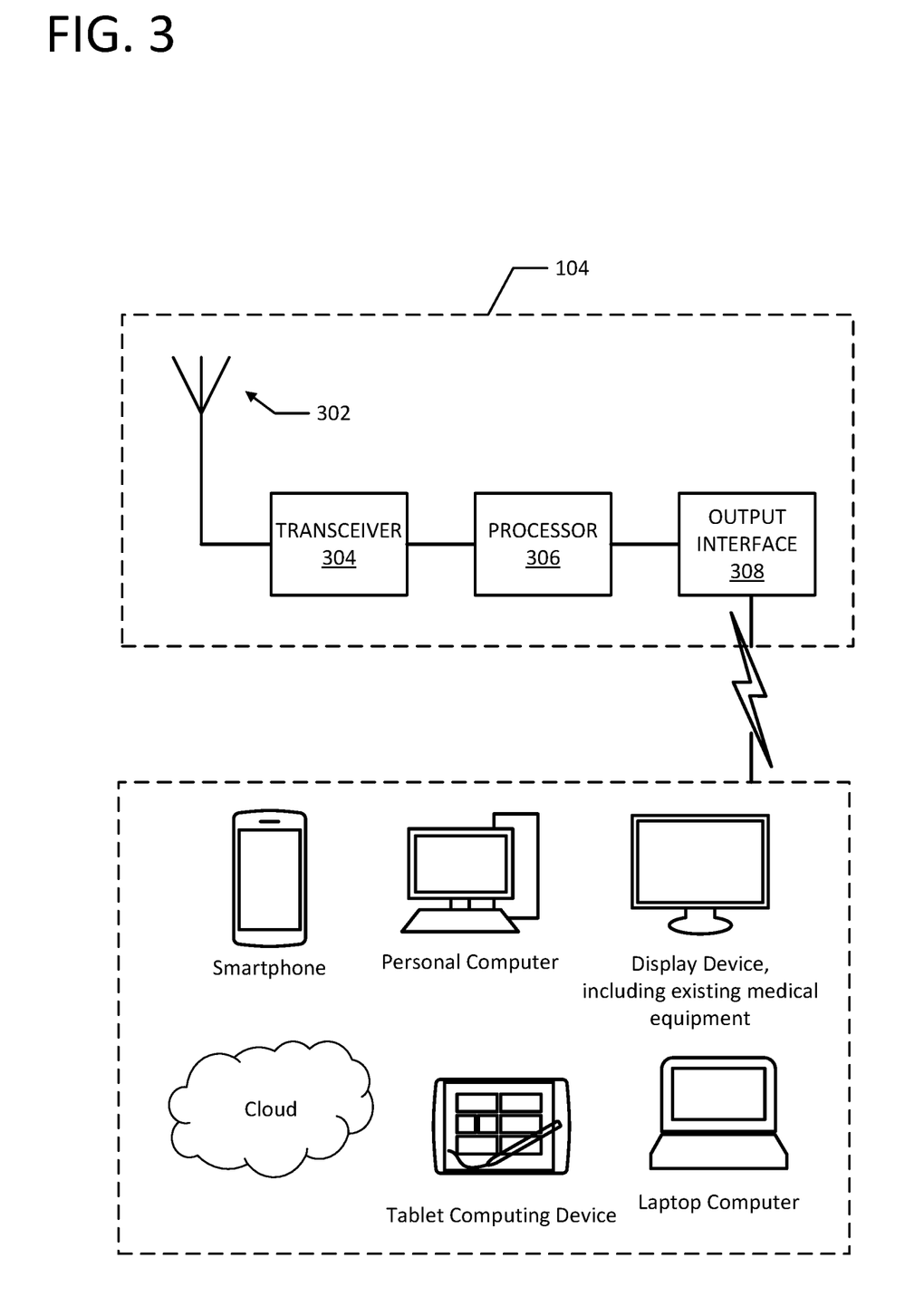
FIG. 3 is a block diagram of a biopotential monitoring system of the hereof, according to an example embodiment.

FIG. 3 is a block diagram illustrating the biopotential monitoring system 104. As illustrated, the biopotential monitoring system 104 includes an antenna 302, a transceiver 304, a processor 306, and an output interface 308. The antenna 302 is electrically and/or communicatively connected to the transceiver 304, which in turn is electrically and/or communicatively connected to the processor 306. The processor 306 is electrically and/or communicatively connected to the output interface 308.

The transceiver 304 is configured to receive alternating currents received from the antenna 302, which is configured to intercept radio waves (e.g., receiving transmissions from antennas of the sensor assemblies 102, etc.) and convert them into the alternating currents. The transceiver 304 is also configured to extract information/data from the alternating currents. The transceiver 304 is further configured to combine digital signals/data packets generated by the processor 306 with an RF signal and apply the modulated signal to the antenna 302, which radiates the energy of the RF signal as radio waves (e.g., transmissions to antennas of the biopotential sensor assemblies 102, etc.).

The processor 306 is configured to generate a continuous-time biopotential (e.g., electrocardiogram, etc.) vector from the sampled biopotential data received from a pair of biopotential sensor assemblies 102. For example, the sampled biopotential data received from the biopotential sensor assembly 102-A may comprise a positive vector and the sampled biopotential data received from the biopotential sensor assembly 102-B may comprise a negative vector, which are combined by the processor 306 to construct an output signal that resembles a typical biopotential measurement signal. The processor 306 is further configured to generate and send synchronization beacons to the biopotential sensor assemblies 102, receive data packets that include the sampled biopotential data, and send acknowledgements to and receive acknowledgements from the biopotential sensor assemblies 102, as further described herein.

The output interface 308 is configured to electrically and/or communicatively interface the biopotential monitoring system 104 to one or more output devices. Exemplary output devices include, but are not limited to, conventional EKG monitors, existing medical equipment, personal computer systems, tablet computing devices, smartphones, and the like. These devices enable the output signals and/or data to be displayed, further analyzed, stored (e.g., in memory devices), and the like. In some embodiments, the output interface 308 is a network interface configured to interface the biopotential monitoring system 104 with a communications network (e.g., local area network, the internet, an intranet, etc.) for communicating the output signals and/or data to remote computing devices and/or a cloud.

Figure 4:
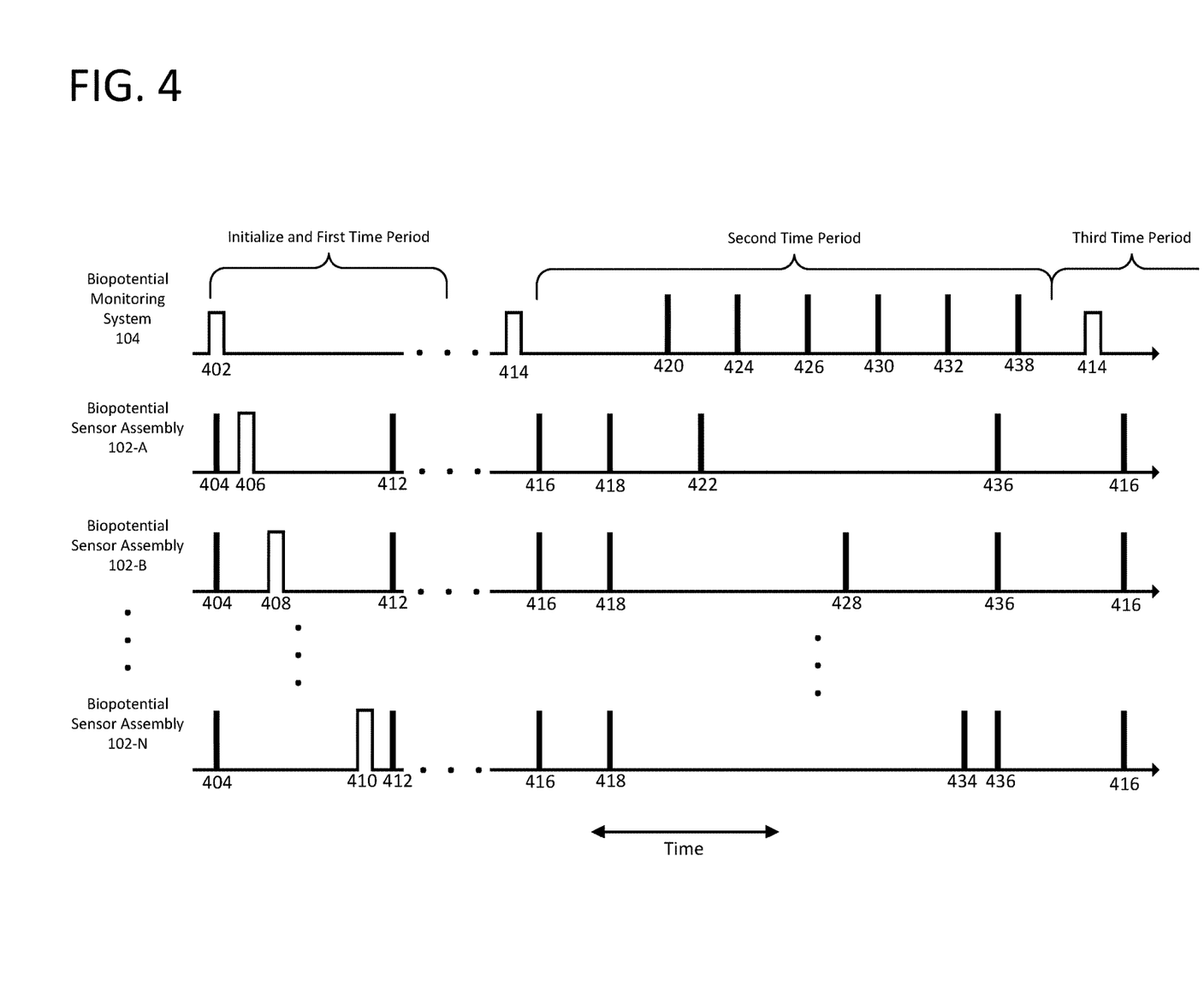
FIG. 4 is a diagram of a sample synchronization method hereof, according to an example embodiment.

FIG. 4 is a diagram illustrating the synchronization of the acquisition of the biopotential signal samples. In an embodiment, synchronization is controlled by the biopotential monitoring system 104. At 402, the biopotential monitoring system 104 transmits a synchronization beacon to the biopotential sensor assemblies 102 via the wireless communications channels 106. In an embodiment, the synchronization beacon is a command initiated by a two-byte sequence followed by a two-byte command. At 404, the biopotential sensor assemblies 102 acquire biopotential signal samples substantially simultaneously. The biopotential sensor assemblies 102-A, 102-B, 102-N each send a unique acknowledgement back to the biopotential monitoring system 104 at 406, 408, and 410, respectively. Upon receiving the acknowledgement from the last biopotential sensor assembly 102-N, the biopotential monitoring system 104 initiates another sample sequence at 412. When the biopotential monitoring system 104 fails to receive an acknowledgement from any one of the biopotential sensor assemblies, it restarts the sequence (e.g., at 402) until each of the biopotential sensor assemblies successfully acknowledges. In an embodiment, steps 402 through 412 comprise an initialization and first time period (e.g., second, etc.).

After the passing of one time period (e.g., one second, etc.), less the time required for one sample, the biopotential monitoring system 104 transmits another synchronization beacon to the biopotential sensor assemblies 102 at 414. In an embodiment, the subsequent synchronization beacons are sent one sample time early (e.g., before the start of the next time period) to enable each biopotential sensor assembly 102 to determine whether it should resynchronize itself or continue the process with the previous synchronization beacon. In some embodiments, the biopotential sensor assemblies 102 stay synchronized for a day or more without the need for a resynchronization beacon.

At the end of each time period, the biopotential sensor assemblies 102 send one time period's worth of samples to the biopotential monitoring system 104. In an embodiment, each data packet sent by the biopotential sensor assemblies 102 is numbered to identify the source and the sequence. The biopotential sensor assemblies 102 are configured to store one or more data packets to ensure sending success. At 416, the biopotential sensor assemblies 102 acquire another set of biopotential signal samples substantially simultaneously. The biopotential sensor assemblies 102 transmit these samples acquired at 416 to the biopotential monitoring system 104 after acquiring yet another set of biopotential signal samples substantially simultaneously at 418.

For example, the biopotential monitoring system 104 requests, at 420, the biopotential signal samples (416) acquired by the biopotential sensor assembly 102-A. At 422, the biopotential sensor assembly 102-A sends the acquired (416) biopotential signal samples with an identifier to the biopotential monitoring system 104. At 424, the biopotential monitoring system 104 acknowledges to the biopotential sensor assembly 102-A that it received the data. When the biopotential monitoring system 104 does not acknowledge receiving the data, the biopotential sensor assembly 102-A will keep the data (e.g., in a memory device) for at least one time period (e.g., one second) to allow the biopotential monitoring system 104 to request the data until it has been received.

These steps are repeated for the biopotential sensor assemblies 102-B through 102-N. The biopotential monitoring system 104 requests, at 426, the biopotential signal samples (416) acquired by the biopotential sensor assembly 102-B. At 428, the biopotential sensor assembly 102-B sends the acquired (416) biopotential signal samples with an identifier to the biopotential monitoring system 104. At 430, the biopotential monitoring system 104 acknowledges to the biopotential sensor assembly 102-B that it received the data. The biopotential monitoring system 104 requests, at 432, the biopotential signal samples (416) acquired by the biopotential sensor assembly 102-N. At 434, the biopotential sensor assembly 102-N sends the acquired (416) biopotential signal samples with an identifier to the biopotential monitoring system 104. At 438, the biopotential monitoring system 104 acknowledges to the biopotential sensor assembly 102-N that it received the data. At 436, the biopotential sensor assemblies 102 acquire another set of biopotential signal samples, which initiates the process for sending the biopotential signal samples acquired at 418 to the biopotential monitoring system 104.

The biopotential sensor assemblies 102 use the synchronization beacon to keep their samples synchronized. If a sensor assembly 102 does not receive the synchronization beacon, it will continue on its sequence based on current timing parameters. When a set recording length is met, the biopotential monitoring system 104 sends out a stop command sequence to end the streaming/recording of data by the biopotential sensor assemblies 102.

Figure 5:
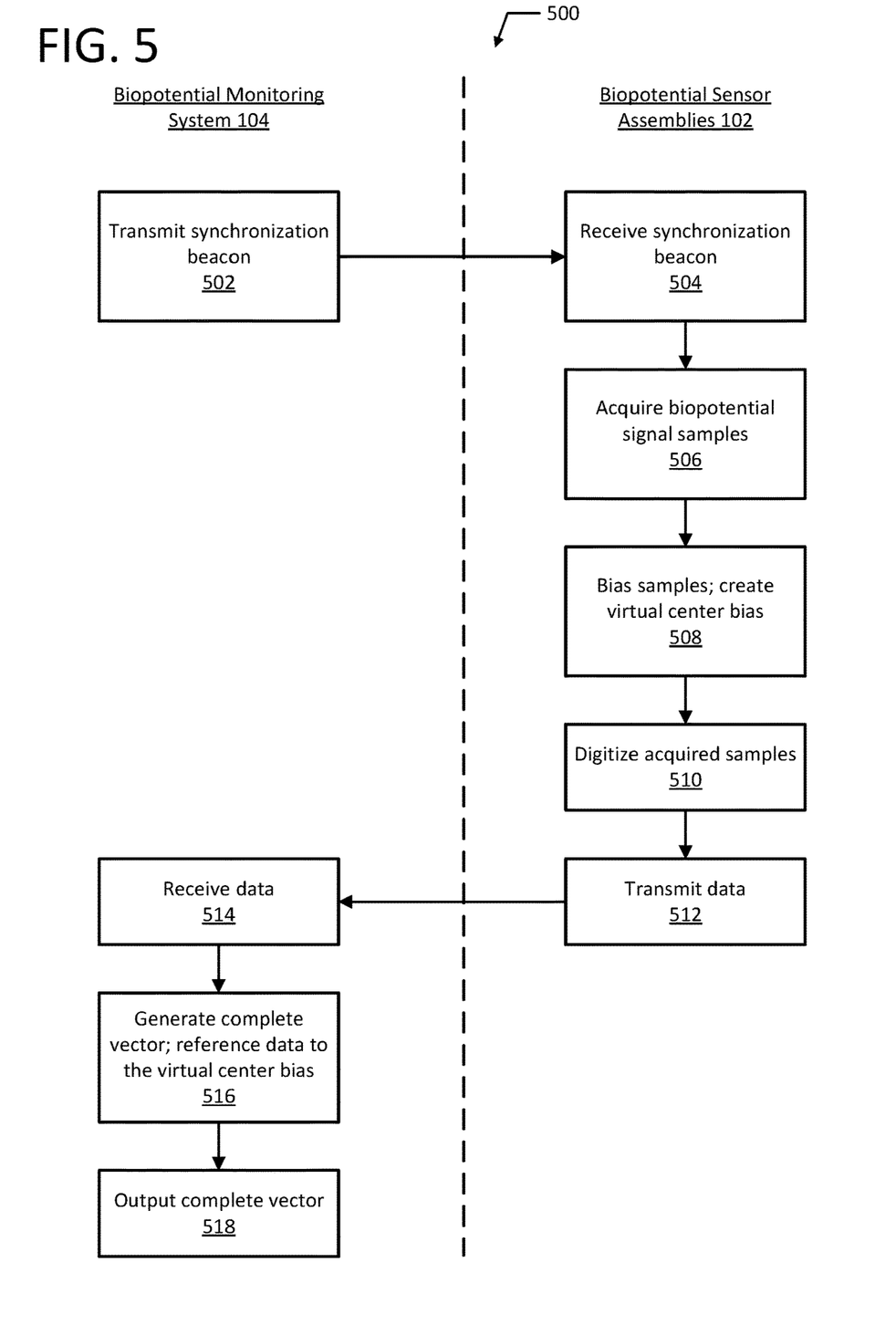
FIG. 5 is a flowchart of a method hereof, according to an example embodiment.

FIG. 5 is a block diagram illustrating an exemplary method 500 of the biopotential system 100. At 502, the biopotential monitoring system 104 transmits a synchronization beacon to all of the biopotential sensor assemblies 102 via the wireless communications channels 106. The biopotential sensor assemblies 102 receive the synchronization beacon at 504 and then simultaneously acquire the biopotential signal samples at 506. As further described herein, acquiring the samples simultaneously achieves a virtual common mode rejection for the acquired samples. At 508, the biopotential sensor assemblies 102 each bias their respective acquired samples and create the virtual center bias that is common to all of the biopotential sensor assemblies 102. The biopotential sensor assemblies 102 digitize the acquired samples at 510 and transmit the data to the biopotential monitoring system 104 at 512 via the wireless communications channels 106. At 514, the biopotential monitoring system 104 receives the data and then generates complete biopotential vectors from the received data at 516. In some embodiments, generating the vectors includes referencing the biopotential data to the virtual center bias that was common to all of the biopotential sensor assemblies 102. At 518, the biopotential monitoring system 104 outputs the generated vectors to one or more computing devices, display devices, communications networks, or the like.

Figure 6:
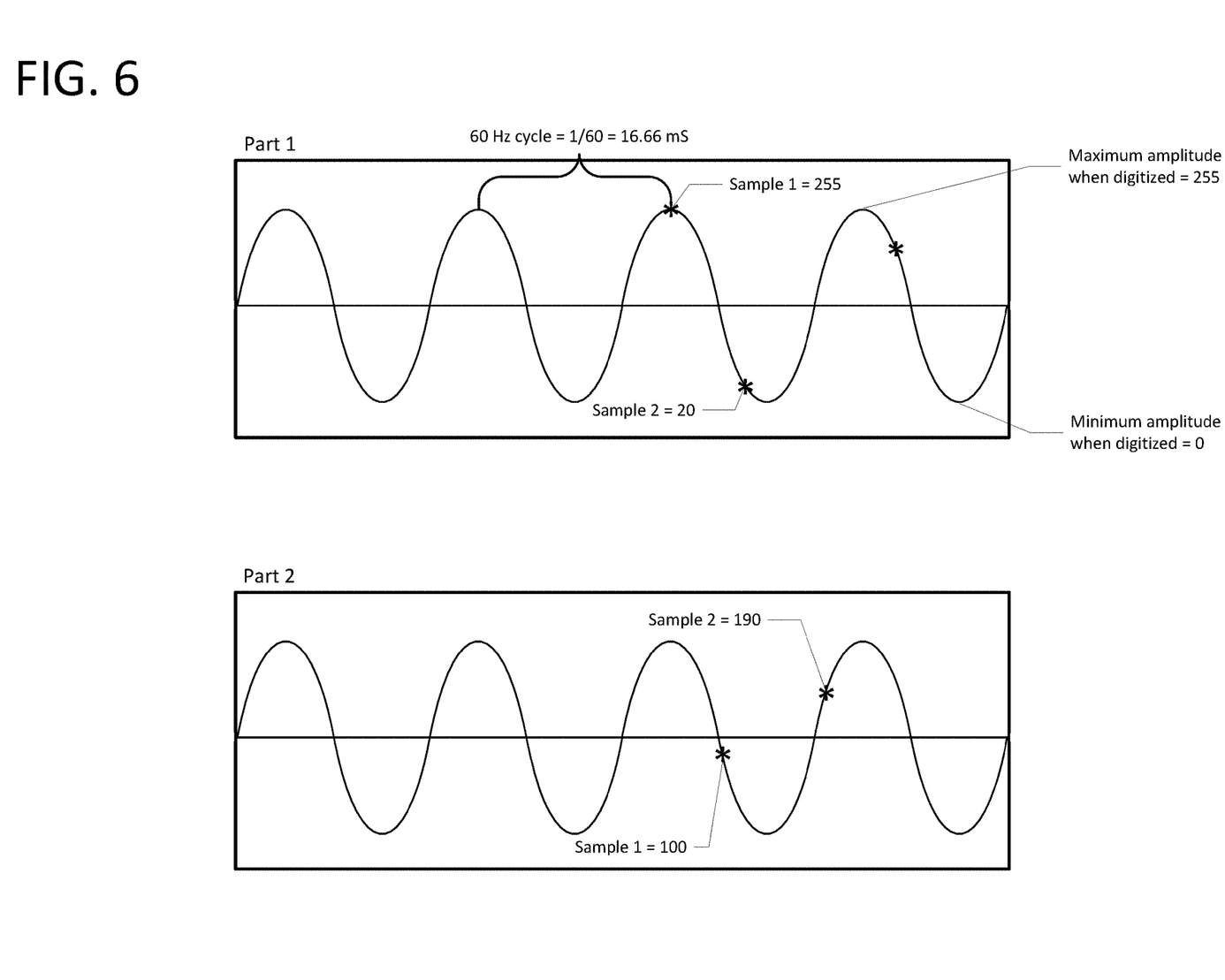
FIG. 6 is a diagram of noise waveforms rejected by systems and methods hereof, according to an example embodiment.

FIG. 6 illustrates the noise magnitude that results from non-synchronized samples, such as in accordance with conventional techniques. Conventional systems cancel noise at the analog level using differential amplifiers. The signals that are the same from two different inputs, such as noise, are canceled out by applying the same signal to both the positive and negative sides of the differential amplifier. The most common noise seen in conventional ECG signals is 50 Hz and 60 Hz. Depending on the application, most conventional ECG equipment samples between 128 samples per second up to 1000 samples per second. The waveforms illustrated in FIG. 6 illustrate an example 60 Hz noise waveform at 8-bit magnitude. Part 1 and Part 2 are not synchronized and the sample rate per channel is 128 (1/128=7.8125 mS). When not synchronized, the resulting data from Part 1 and Part 2 is as follows:

(Part 1,Sample 1)−(Part 2,Sample 1)=255−100=155 noise magnitude (Part 1,Sample 2)−(Part 2,Sample 2)=20−190=−170 noise magnitude When synchronized, the resulting data from Part 1 and Part 2 is as follows:

(Part 1,Sample 1)−(Part 2,Sample 1)=255−255=0 noise magnitude (Part 1,Sample 2)−(Part 2,Sample 2)=20−20=0 noise magnitude As illustrated in FIG. 6, only 2.1248 samples will fit inside the 60 Hz wave. If the samples are not synchronized, then the worst case scenario is the noise would be amplified and not canceled out. When the data is synchronized, then a virtual common mode rejection is achieved.

Although embodiments are described herein in connection with biopotential signal measurements in the form of electrocardiographs (EKG or ECG), one having ordinary skill in the art will understand that the systems, methods, and techniques described herein are applicable with any biological parameter that utilizes a differential signal. For example, the systems, methods, and techniques described herein can be used for measurement and recording of electrophysiological activity including, but not limited to, electroencephalography (EEG), electromyography (EMG), electrical brain stimulation (EBS), and the like.

As is evident from the foregoing description, certain aspects of the present inventions are not limited by the particular details of the examples illustrated herein, and it is therefore contemplated that other modifications, applications, variations, or equivalents thereof, will occur to those skilled in the art. Many such changes, modifications, variations and other uses and applications of the present constructions will, however, become apparent to those skilled in the art after considering the specification and the accompanying drawings. All such changes, modifications, variations and other uses in applications which do not depart from the spirit and scope of the present inventions are deemed to be covered by the inventions which are limited only by the claims which follow.

What is claimed is:

1. A system, comprising:
a first biopotential sensor assembly, comprising:
a first interface configured to electrically interface the first biopotential sensor assembly with a first electrode for acquiring first biopotential signal samples based on a synchronization beacon,
a plurality of first resistors configured to create a first virtual center bias within the first biopotential sensor assembly,
a first processor configured to convert the first biopotential signal samples into first digital biopotential data, and
a first transceiver configured to wirelessly receive the synchronization beacon and wirelessly transmit the first digital biopotential data,
a first electric power source, and
a first operational amplifier configured to amplify the first biopotential signal sample, the first operational amplifier being coupled to the plurality of first resistors and a first electrical ground,
wherein the first biopotential sensor assembly is configured to electrically interface with no more than one electrode;
a second biopotential sensor assembly that is electrically isolated from the first biopotential sensor assembly, comprising:
a second interface configured to electrically interface the second biopotential sensor assembly with a second electrode for acquiring second biopotential signal samples based on the synchronization beacon,
a plurality of second resistors configured to create a second virtual center bias within the second biopotential sensor assembly,
a second processor configured to convert the second biopotential signal samples into second digital biopotential data, and a second transceiver configured to wirelessly receive the synchronization beacon and wirelessly transmit the second digital biopotential data, a second electric power source, wherein the second electric power source is isolated from the first electric power source, and a second operational amplifier configured to amplify the second biopotential signal sample, the second operational amplifier being coupled to the plurality of second resistors and a second electrical ground, wherein the first biopotential sensor assembly and the second biopotential sensor assembly operate independently from one another and the second biopotential sensor assembly is configured to electrically interface with no more than one electrode; and a biopotential monitoring system, comprising:

a third transceiver configured to wirelessly receive the first and second digital biopotential data and wirelessly transmit the synchronization beacon, and a third processor configured to:

generate the synchronization beacon for synchronizing the acquisition of the first and second biopotential signal samples by the first and second biopotential sensor assemblies, and generate one or more complete electrocardiogram vectors from the first and second digital biopotential data.

2. The system of claim 1, wherein the second electrical ground is isolated from the first electrical ground.

3. The system of claim 1, wherein the first biopotential sensor assembly comprises a positive electrocardiogram (ECG) vector, and wherein the second biopotential sensor assembly comprises a negative ECG vector.

4. The system of claim 1, wherein neither the first biopotential sensor assembly nor the second biopotential sensor assembly comprises a reference electrode.

5. The system of claim 1, wherein the first and second biopotential sensor assemblies are adapted to be applied to a body of a patient.

6. The system of claim 5, wherein the first and second biopotential sensor assemblies are physically isolated from each other.

7. The system of claim 1, wherein the first biopotential sensor assembly further comprises a first AC coupling capacitor configured to remove one or more direct current components from the first biopotential signal sample, and wherein the second biopotential sensor assembly further comprises a second AC coupling capacitor configured to remove one or more direct current components from the second biopotential signal sample.

8. The system of claim 1, wherein the first processor is further configured to insert a first identifier that uniquely identifies the first biopotential sensor assembly into the first digital biopotential data, and wherein the second processor is further configured to insert a second identifier that uniquely identifies the second biopotential sensor assembly into the second digital biopotential data.

* * * * *